US007210994B1

(12) United States Patent
Donohue

(10) Patent No.: US 7,210,994 B1
(45) Date of Patent: May 1, 2007

(54) VACUUM BAG WITH A VALVE ADAPTED TO HOLD FLUIDS

(76) Inventor: Shannon E. Donohue, 1051 Shelburne Dr., Franklin Square, NY (US) 11010-1032

( * ) Notice: Subject to any disclaimer, the term of this patent is extended or adjusted under 35 U.S.C. 154(b) by 0 days.

(21) Appl. No.: 11/444,232

(22) Filed: May 30, 2006

(51) Int. Cl.
A22B 5/00 (2006.01)
(52) U.S. Cl. ..................................... 452/198
(58) Field of Classification Search ................. 452/198
See application file for complete search history.

(56) References Cited

U.S. PATENT DOCUMENTS 4,466,888 A * 8/1984 Verkaart ..................... 210/232
5,178,300 A * 1/1993 Haviv et al. .................. 222/95
5,810,202 A * 9/1998 Hoback et al. ............... 222/95
5,881,881 A * 3/1999 Carrington ............... 206/524.8
5,913,232 A * 6/1999 Betts et al. .................. 73/1.03
5,961,210 A * 10/1999 McCardel et al. .......... 366/130
6,059,457 A * 5/2000 Sprehe et al. ................. 383/63

* cited by examiner

Primary Examiner—Thomas Price

(57) ABSTRACT

A viscera bag includes a closure and a valve connection. The bag is flexible and a vacuum line can be connected thereto. The vacuum line can withdraw fluids from the bag and the bag can be vacuum sealed to ensure that fluids will not leak out of the bag. A method of performing an autopsy includes using the viscera bag to contain any organs that have been removed and placing the removed organs in the bag back into the body after fluid has been withdrawn from the bag.

1 Claim, 1 Drawing Sheet

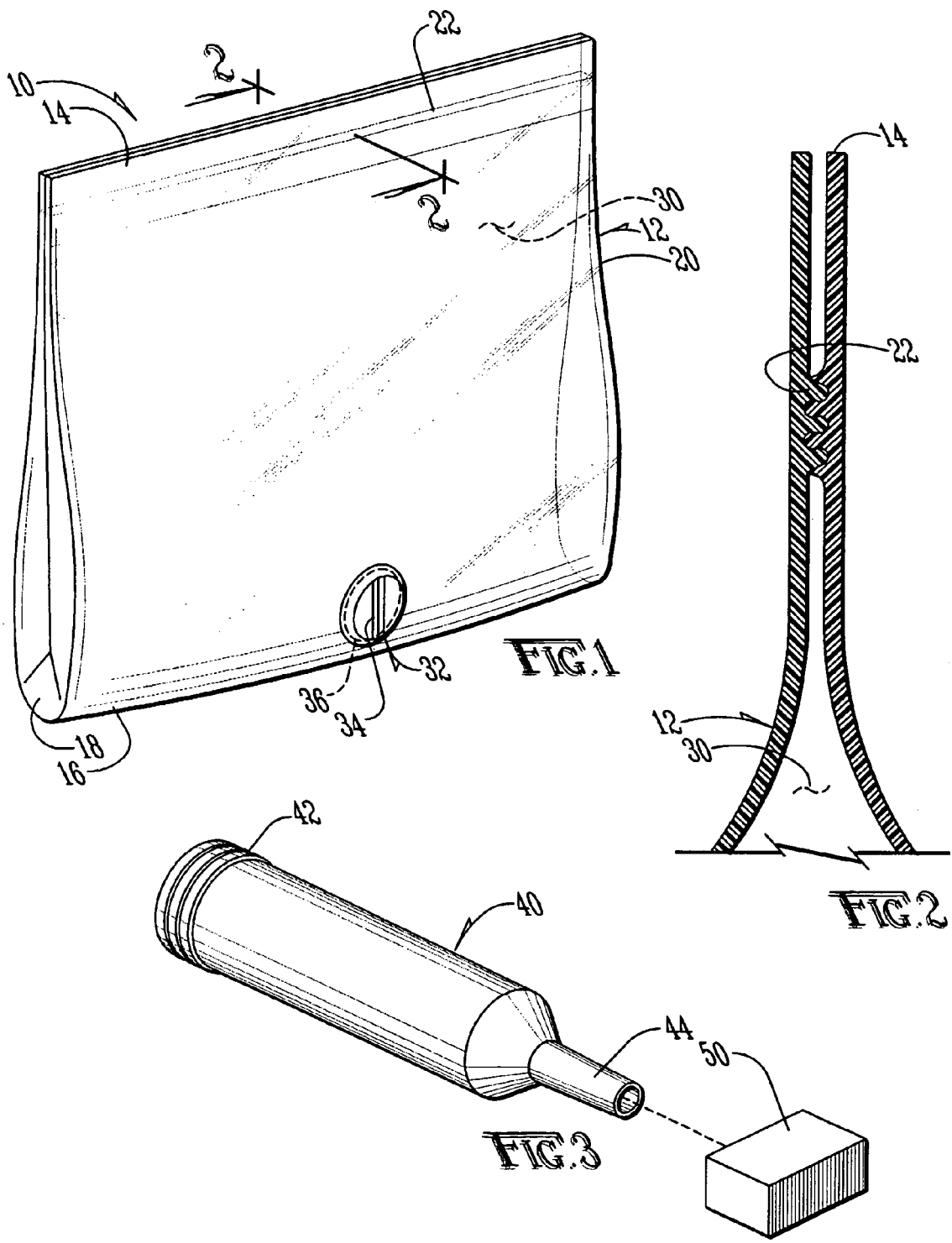

VACUUM BAG WITH A VALVE ADAPTED TO HOLD FLUIDS

TECHNICAL FIELD OF THE INVENTION

The present invention relates to the general art of special containers, and to the particular field of autopsy and post mortem examinations.

BACKGROUND OF THE INVENTION

Many jurisdictions require an autopsy to be performed to assure that death was from natural or accidental causes, and an autopsy is sometimes requested or permitted by the family of the deceased, even though not legally required. It is not unusual for a Medical Examiners' office, in an urban area, to perform a number of autopsy examinations a day.

During the autopsy, a medical examiner may perform different procedures on a person's body to determine the cause of death and other medical information that may not have been known during the person's life. Incisions may be made to the skull and chest and organs such as the brain, the stomach, the kidneys, the liver and the heart may be detached and lifted out of the body. The organs are examined and weighted then tissue samples may be taken for further examination. Finally, the organs are placed in a viscera bag and replaced inside the body, the incisions are sewn shut and the person's body is prepared for burial or cremation.

However, some body fluids often remain in the body organs that have been removed from the body and placed in the viscera bag. As a result, leaks can occur with the viscera bag which can be undesirable.

Therefore, there is a need for a viscera bag that can contain organs and the like without leakage.

SUMMARY OF THE INVENTION

The above-discussed disadvantages of the prior art are overcome by a viscera bag and a method of performing an autopsy using such viscera bag. The bag includes a built-in valve which will allow body organs inside the bag to be drained of body fluids. The bag can be vacuum sealed to prevent any possible leaking and would save time and would provide great convenience for users.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWING FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a perspective view of a viscera bag embodying the present invention.

FIG. 2 is a sectional view taken along line 2—2 of FIG. 1.

FIG. 3 is a vacuum tube that can be attached to the viscera bag shown in FIG. 1 to apply a vacuum seal and to withdraw fluids from the bag.

DETAILED DESCRIPTION OF THE INVENTION

Referring to the figures, it can be understood that the present invention is embodied in a viscera bag 10 which overcomes the above-discussed disadvantages. Bag 10 comprises a flexible body 12 which can be formed of translucent or transparent material. Body 12 is a closable bag and has a first end 14 which is a top end when the body is in use and a second end 16 which is a bottom end when the body is in use. Body 12 further includes a first side wall 18 and a second side wall 20.

A closure seal 24 is located on the first end and serves to close the first side wall to the second side wall when in use. The closure seal can be a ziplock type closure. An inside volume 30 is defined by the side walls of the bag. A fluid outlet port 32 is defined in the first side wall, and a one-way valve 34 is mounted on the first side wall in the fluid outlet port. A mesh screen 36 is mounted on the first side wall to cover the one-way valve. The mesh screen prevents solid particles from clogging the one-way valve.

The one-way valve allows fluid to exit the bag from the inside volume but prevents fluid from entering the bag into the inside volume. A fluid conduit 40 has a first end 42 which is sized and adapted to connect to the one-way valve to fluidically connect the fluid conduit to the inside volume of the bag and a second end 44 which is sized and adapted to be fluidically connected to a fluid suction system 50. Any suitable fluid suction system can be used without departing from the scope of the present disclosure. The details of the fluid suction system are not important to the present invention and will not be claimed. As such the details of the fluid suction system will not be presented.

The present invention is further embodied in a method of performing an autopsy. The method of performing an autopsy embodying the present invention comprises making incisions in various parts of a body being examined; removing organs from the body for examination; examining the removed organs; providing a viscera bag comprising a flexible body having a first end which is a top end when the body is in use, a second end which is a bottom end when the body is in use, a first side wall, a second side wall, a closure seal on the first end closing the first side wall to the second side wall when in use, and an inside volume defined by the side walls of the bag; a fluid outlet port defined in the first side wall; a one-way valve mounted on the first side wall in the fluid outlet port; a mesh screen mounted on the first side wall to cover the one-way valve; and a fluid conduit having a first end which is sized and adapted to connect to the one-way valve to fluidically connect the fluid conduit to the inside volume of the bag, and a second end which is sized and adapted to be fluidically connected to a fluid suction system; after completing examination of the removed organs, placing the removed organs in the viscera bag; sealing the top end of the viscera bag using the closure seal; connecting the viscera bag containing the removed organs to the suction system via the one-way valve and the fluid conduit; using the suction system, applying suction to the viscera bag and removing fluid from the viscera bag; removing the viscera bag from the suction system; replacing the viscera bag inside the body; and sewing the incisions shut. The body can then be sent to the appropriate location for further processing, such as preparation for burial or cremation. The use of the viscera bag will prevent fluid leakage during such transport and preparation.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

What is claimed is:

1. A method of performing an autopsy comprising:
   A) making incisions in various parts of a body being examined;
   B) removing organs from the body for examination;
   C) examining the removed organs;
   D) providing a viscera bag comprising a flexible body having a first end which is a top end when the body is in use, a second end which is a bottom end when the body is in use, a first side wall, a second side wall, a closure seal on the first end closing the first side wall to the second side wall when in use, and an inside volume defined by the side walls of the bag; a fluid outlet port defined in the first side wall; a one-way valve mounted on the first side wall in the fluid outlet port; a mesh screen mounted on the first side wall to cover the one-way valve; and a fluid conduit having a first end which is sized and adapted to connect to the one-way valve to fluidically connect the fluid conduit to the inside volume of the bag, and a second end which is sized and adapted to be fluidically connected to a fluid suction system;
   E) after completing examination of the removed organs, placing the removed organs in the viscera bag;
   F) sealing the top end of the viscera bag using the closure seal;
   G) connecting the viscera bag containing the removed organs to the suction system via the one-way valve and the fluid conduit;
   H) using the suction system, applying suction to the viscera bag and removing fluid from the viscera bag;
   I) removing the viscera bag from the suction system;
   J) replacing the viscera bag inside the body; and
   K) sewing the incisions shut.

* * * * *